(12) United States Patent
Hanina et al.

(10) Patent No.: US 10,762,172 B2
(45) Date of Patent: Sep. 1, 2020

(54) APPARATUS AND METHOD FOR OBJECT CONFIRMATION AND TRACKING

(75) Inventors: Adam Hanina, New York, NY (US); Gordon Kessler, Mt. Kisco, NY (US); Lei Guan, Philadelphia, PA (US)

(73) Assignee: Ai Cure Technologies LLC, Mount Kisco, NY (US)

( * ) Notice: Subject to any disclaimer, the term of this patent is extended or adjusted under 35 U.S.C. 154(b) by 29 days.

(21) Appl. No.: 12/898,338

(22) Filed: Oct. 5, 2010

(65) Prior Publication Data

US 2012/0084091 A1 Apr. 5, 2012

(51) Int. Cl.
| | | |
|---|---|---|
| G06F 19/00 | (2018.01) | |
| G06Q 99/00 | (2006.01) | |
| G16H 20/10 | (2018.01) | |
| G06Q 50/22 | (2018.01) | |
| G06K 9/00 | (2006.01) | |
| G06T 7/246 | (2017.01) | |

(52) U.S. Cl.
CPC ..... *G06F 19/3456* (2013.01); *G06K 9/00577* (2013.01); *G06Q 50/22* (2013.01); *G06Q 99/00* (2013.01); *G06T 7/246* (2017.01); *G16H 20/10* (2018.01); *G06T 2207/20016* (2013.01)

(58) Field of Classification Search
USPC .................. 382/118, 190; 705/2, 3
See application file for complete search history.

(56) References Cited

U.S. PATENT DOCUMENTS

| | | |
|---|---|---|
| 3,814,845 A | 6/1974 | Hurlbrink et al. |
| 5,065,447 A | 11/1991 | Barnsley et al. |
| 5,441,047 A | 8/1995 | David et al. |
| 5,544,649 A | 8/1996 | David et al. |
| 5,619,991 A | 4/1997 | Sloane |
| 5,646,912 A | 7/1997 | Cousin |
| 5,752,621 A | 5/1998 | Passamante |
| 5,764,296 A | 6/1998 | Shin |

(Continued)

FOREIGN PATENT DOCUMENTS

| | | |
|---|---|---|
| WO | PCT/US10/56935 | 11/2010 |
| WO | PCT/US11/35093 | 5/2011 |

(Continued)

OTHER PUBLICATIONS

Christensen, Arne et al., Electronic monitoring of patient adherence to oral antihypertensive medical treatment: a systematic review, Journal of Hypertension: Aug. 2009—vol. 27—Issue 8—p. 1540-1551 (Year: 2009).*
"PCT Search report and written opinion", (dated Jan. 12, 2011),1-9.
"Non-Final Office Action from PTO", (dated Oct. 13, 2011),1-74.

(Continued)

*Primary Examiner* — Aryan E Weisenfeld
*Assistant Examiner* — Joshua B Blanchette
(74) *Attorney, Agent, or Firm* — Fish & Richardson P.C.

(57) ABSTRACT

A method and apparatus for tracking a medication to be administered by a user. The method includes the steps of determining the identity of a medication to be administered by a user, identifying one or more characteristics associated with the medication that are to be used to continue to track the medication, the one or more characteristics including less than a total number of characteristics associated with the medication to be administered, and tracking the medication to be administered in accordance with the identified one or more characteristics through one or more future video images.

25 Claims, 6 Drawing Sheets

(56) References Cited

U.S. PATENT DOCUMENTS

| | | |
|---|---|---|
| 5,810,747 A | 9/1998 | Brudny et al. |
| 5,911,132 A | 6/1999 | Sloane |
| 5,961,446 A | 10/1999 | Beller et al. |
| 6,151,521 A | 11/2000 | Guo et al. |
| 6,233,428 B1 | 5/2001 | Fryer |
| 6,283,761 B1 | 9/2001 | Joao |
| 6,380,858 B1 | 4/2002 | Yarin et al. |
| 6,409,661 B1 | 6/2002 | Murphy |
| 6,421,650 B1 | 7/2002 | Goetz et al. |
| 6,483,993 B1 | 11/2002 | Misumi et al. |
| 6,484,144 B2 | 11/2002 | Martin et al. |
| 6,535,637 B1* | 3/2003 | Wootton ............. B65B 57/00 382/190 |
| 6,611,206 B2 | 8/2003 | Eshelman et al. |
| 6,705,991 B2 | 3/2004 | Bardy |
| 6,879,970 B2 | 11/2005 | Shiffman et al. |
| 6,988,075 B1 | 1/2006 | Hacker |
| 7,184,047 B1 | 2/2007 | Crampton |
| 7,184,075 B2 | 2/2007 | Reiffel |
| 7,256,708 B2 | 8/2007 | Rosenfeld et al. |
| 7,277,752 B2 | 10/2007 | Matos |
| 7,304,228 B2 | 12/2007 | Bryden et al. |
| 7,307,543 B2 | 12/2007 | Rosenfeld et al. |
| 7,317,967 B2 | 1/2008 | DiGianfilippo et al. |
| 7,340,077 B2 | 3/2008 | Gokturk |
| 7,395,214 B2 | 7/2008 | Shillingburg |
| 7,415,447 B2 | 11/2008 | Shiffman et al. |
| 7,448,544 B1 | 11/2008 | Louie et al. |
| 7,562,121 B2 | 7/2009 | Berisford et al. |
| 7,627,142 B2 | 12/2009 | Kurzweil et al. |
| 7,657,443 B2 | 2/2010 | Crass et al. |
| 7,692,625 B2 | 4/2010 | Morrison et al. |
| 7,747,454 B2 | 6/2010 | Bartfeld et al. |
| 7,761,311 B2 | 7/2010 | Clements et al. |
| 7,769,465 B2 | 8/2010 | Matos |
| 7,774,075 B2 | 8/2010 | Lin et al. |
| 7,874,984 B2 | 1/2011 | Elsayed et al. |
| 7,881,537 B2 | 2/2011 | Ma et al. |
| 7,908,155 B2 | 3/2011 | Fuerst et al. |
| 7,912,733 B2 | 3/2011 | Clements et al. |
| 7,956,727 B2 | 6/2011 | Loncar |
| 7,983,933 B2 | 7/2011 | Karkanias et al. |
| 8,321,284 B2 | 11/2012 | Clements et al. |
| 2001/0049673 A1 | 12/2001 | Dulong et al. |
| 2001/0056358 A1 | 12/2001 | Dulong et al. |
| 2002/0026330 A1 | 2/2002 | Klein |
| 2002/0093429 A1 | 7/2002 | Matsushita et al. |
| 2002/0143563 A1 | 10/2002 | Hufford et al. |
| 2003/0164172 A1 | 9/2003 | Chumas et al. |
| 2003/0190076 A1 | 10/2003 | Delean |
| 2003/0225325 A1 | 12/2003 | Kagermeier et al. |
| 2004/0100572 A1 | 5/2004 | Kim |
| 2004/0107116 A1 | 6/2004 | Brown |
| 2004/0155780 A1 | 8/2004 | Rapchak |
| 2005/0144150 A1 | 6/2005 | Ramamurthy et al. |
| 2005/0149361 A1 | 7/2005 | Saus et al. |
| 2005/0180610 A1* | 8/2005 | Kato ............. G06K 9/00275 382/118 |
| 2005/0182664 A1 | 8/2005 | Abraham-Fuchs et al. |
| 2005/0234381 A1 | 10/2005 | Niemetz et al. |
| 2005/0267356 A1 | 12/2005 | Ramasubramanian et al. |
| 2006/0066584 A1 | 3/2006 | Barkan |
| 2006/0218011 A1 | 9/2006 | Walker et al. |
| 2006/0238549 A1 | 10/2006 | Marks |
| 2007/0008112 A1 | 1/2007 | Covannon et al. |
| 2007/0008113 A1 | 1/2007 | Spoonhower et al. |
| 2007/0030363 A1 | 2/2007 | Cheatle et al. |
| 2007/0118389 A1 | 5/2007 | Shipon |
| 2007/0194034 A1 | 8/2007 | Vasiadis |
| 2007/0233035 A1 | 10/2007 | Wehba et al. |
| 2007/0233049 A1 | 10/2007 | Wehba et al. |
| 2007/0233050 A1 | 10/2007 | Wehba et al. |
| 2007/0233281 A1 | 10/2007 | Wehba et al. |
| 2007/0233520 A1 | 10/2007 | Wehba et al. |
| 2007/0233521 A1 | 10/2007 | Wehba et al. |
| 2007/0260487 A1* | 11/2007 | Bartfeld ............... G06Q 30/018 705/2 |
| 2007/0273504 A1 | 11/2007 | Tran |
| 2008/0000979 A1 | 1/2008 | Poisner |
| 2008/0162192 A1 | 3/2008 | Vonk et al. |
| 2008/0093447 A1 | 4/2008 | Johnson et al. |
| 2008/0114226 A1 | 5/2008 | Music et al. |
| 2008/0114490 A1 | 5/2008 | Jean-Pierre |
| 2008/0138604 A1 | 6/2008 | Kenney et al. |
| 2008/0140444 A1 | 6/2008 | Karkanias et al. |
| 2008/0178126 A1 | 7/2008 | Beeck et al. |
| 2008/0201174 A1 | 8/2008 | Ramasubramanian et al. |
| 2008/0219493 A1 | 9/2008 | Tadmor |
| 2008/0275738 A1 | 11/2008 | Shillingburg |
| 2008/0290168 A1 | 11/2008 | Sullivan et al. |
| 2008/0297589 A1 | 12/2008 | Kurtz et al. |
| 2008/0303638 A1 | 12/2008 | Nguyen et al. |
| 2009/0012818 A1* | 1/2009 | Rodgers ............... G06F 19/3462 705/3 |
| 2009/0018867 A1 | 1/2009 | Reiner |
| 2009/0043610 A1 | 2/2009 | Nadas et al. |
| 2009/0048871 A1 | 2/2009 | Skomra |
| 2009/0095837 A1 | 4/2009 | Lindgren |
| 2009/0128330 A1 | 5/2009 | Monroe |
| 2009/0159714 A1 | 6/2009 | Coyne, III et al. |
| 2009/0217194 A1 | 8/2009 | Martin et al. |
| 2009/0245655 A1 | 10/2009 | Matsuzaka |
| 2010/0042430 A1 | 2/2010 | Bartfeld |
| 2010/0050134 A1 | 2/2010 | Clarkson |
| 2010/0057646 A1 | 3/2010 | Martin et al. |
| 2010/0092093 A1 | 4/2010 | Akatsuka et al. |
| 2010/0136509 A1 | 6/2010 | Mejer et al. |
| 2010/0138154 A1 | 6/2010 | Kon |
| 2010/0255598 A1 | 10/2010 | Melker |
| 2010/0262436 A1 | 10/2010 | Chen et al. |
| 2010/0316979 A1 | 12/2010 | Von Bismarck |
| 2011/0021952 A1 | 1/2011 | Vallone |
| 2011/0119073 A1 | 5/2011 | Hanina et al. |
| 2011/0153360 A1 | 6/2011 | Hanina et al. |
| 2011/0161109 A1 | 6/2011 | Pinsonneault et al. |
| 2011/0195520 A1 | 8/2011 | Leider et al. |
| 2011/0275051 A1 | 11/2011 | Hanina et al. |
| 2012/0075464 A1 | 3/2012 | Derenne et al. |

FOREIGN PATENT DOCUMENTS

| | | |
|---|---|---|
| WO | PCT/US11/54666 | 10/2011 |
| WO | PCT/US11/54668 | 10/2011 |
| WO | PCT/US12/41785 | 6/2012 |
| WO | PCT/US12/42843 | 6/2012 |
| WO | PCT/US12/51554 | 8/2012 |
| WO | PCT/US12/51659 | 8/2012 |

OTHER PUBLICATIONS

Non-Final Office Action from PTO, (U.S. Appl. No. 12/620,686), (dated Dec. 21, 2011),1-78.
Final Office Action from PTO, (U.S. Appl. No. 12/620,686), (dated May 8, 2012), 1-24.
International Preliminary Report on Patentability, (PCT/US2010/056935) (dated May 31, 2012), 1-8.
Non-Final Office Action from PTO, (U.S. Appl. No. 12/646,383), (dated Dec. 22, 2011),1-78.
Final Office Action from PTO, (U.S. Appl. No. 12/646,383), (dated May 8, 2012), 1-31.
Final Office Action from PTO, (U.S. Appl. No. 12/646,603), (dated Feb. 1, 2012), 1-17.
Non Final Office Action from PTO, (U.S. Appl. No. 12/728,721), (dated Jan. 6, 2012), 1-31.
Final Office Action from PTO, (U.S. Appl. No. 12/728 721), (dated Apr. 12, 2012), 1-31.
Non-Final Office Action from PTO, (U.S. Appl. No. 12/815,037), (dated Mar. 28, 2012),1-17.
PCT Search report and written opinion, (PCT/US2011/35093, (dated Sep. 12, 2011),1-8.
PCT Search report and written opinion, (PCT/US12/41785, (dated Aug. 17, 2012),1-10.

(56) References Cited

OTHER PUBLICATIONS

U.S. Appl. No. 12/620,686.
U.S. Appl. No. 13/558,377.
U.S. Appl. No. 12/646,383.
U.S. Appl. No. 13/558,380.
U.S. Appl. No. 12/646,603.
U.S. Appl. No. 12/728,721.
U.S. Appl. No. 12/815,037.
U.S. Appl. No. 12/898,338.
U.S. Appl. No. 12/899,510.
U.S. Appl. No. 13/036,210.
U.S. Appl. No. 13/110,500.
U.S. Appl. No. 13/189,518.
U.S. Appl. No. 13/235,387.
U.S. Appl. No. 13/214,201.
U.S. Appl. No. 13/369,757.
U.S. Appl. No. 13/216,099.
Non-Final Office Action from PTO, (U.S. Appl. No. 13/558,377), (daetd Oct. 22, 2012), 1-21.
Final Office Action from PTO, (U.S. Appl. No. 13/558,377), dated May 7, 2013, 1-29.
Non-Final Office Action from PTO, (U.S. Appl. No. 13/558,380), (dated Oct. 4, 2012), 1-20.
Wang et al. "Recent Developments in human motion analysis." Pattern Recognition 36 (220) 585-601 (Nov. 2001).
Final Office Action from PTO, (U.S. Appl. No. 13/588,380), (dated Mar. 1, 2013), 1-27.
Non-Final Office Action from PTO, (U.S. Appl. No. 12/646,603), (dated Jun. 13, 2013), 1-16.
Non-Final Office Action from PTO, (U.S. Appl. No. 12/728,721), (dated May 9, 2013), 1-25.
Final Office Action from PTO, (U.S. Appl. No. 12/815,037), (dated Sep. 13, 2012), 1-15.
Non-Final Office Action from PTO, (U.S. Appl. No. 12/815,037), (dated Jul. 18, 2013), 1-19.
Non-Final Office Action from PTO, (U.S. Appl. No. 12/899,510), (dated Jan. 23, 2013), 1-20.
Final Office Action from PTO, (U.S. Appl. No. 12/899 510), (dated Aug. 28, 2013).
PCT Search report and written opinion, (PCT/US11/54666), (dated Feb. 28, 2012), 1-13.
PCT Search report and written opinion, (PCT/US11/54668), dated Feb. 28, 2012, 1-12.
Non-Final Office Action from PTO, (U.S. Appl. No. 13/189 518), (dated Dec. 21, 2012), 1-10.
Final Office Action from PTO, (U.S. Appl. No. 13/189,518), (dated Jul. 23, 2013), 1-16.
Non-Final Office Action from PTO, (U.S. Appl. No. 13/235,387), dated Sep. 12, 2013), 1-16.
PCT Search report and written opinion, (PCT/US12/42843), (dated Aug. 31, 2012), 1-8.
PCT Search report and written opinion, (PCT/US2012/051554), (dated Oct. 19, 2012), 1-12.
Huynh et al., "Real time detection, tracking and recognition of medication intake." World Academy of Science, Engineering and Technology 60 (2009), 280-287.
PCT Search report and written opinion, (PCT/US12/59139), (dated Dec. 18, 2012), 1-15.
PCT Search report and written Opinion, (PCT/US13/20026), (dated Aug. 5, 2013), 1-14.
Ammouri, S.; Biloduau, G. -A, "Face and Hands Detectionand Tracking Applied to the Monitoring of Medication Intake," Computer and Robot Vision, 2008. CRV '08. Canadian Conference on, vol. No., pp. 147, 154, May 28-30, 2008.
Batz, et al. "A computer Vision System for Monitoring Medicaiton Intake," in Proc. IEEE 2nd Canadian Conf. on Computer and Robot Vision, Victoria, BC, Canada, 2005, pp. 362-369.
Valin, et al. "Video Surveillance of Medication Intake", Int. Conf. of the IEEE Engineering in Medicine and Biology Society, New York City, USA, Aug. 2006.
Bilodeau et al. Monitoring of Medication Intake Using a Camera System. Journal of Medical Systems 2011. [retrieved on Feb. 18, 2013] Retrieved from ProQuest Technology Collection.
Mintchell, "Exploring the Limits of Machine Vision", Automating World, Oct. 1, 2011.
University of Texas, *GuideView*, Mar. 15, 2007, http://www.sahs.uth.tmc.edu/MSriram/GuideView/.
Whitecup, Morris S., *2008 Patient Adherence Update: New Approaches for Success*, Guideline Trend Report, Oct. 2008.
Osterberg, Lars and Blaschke, Terrence, *Adherence to Medication*, New England Journal of Medicine 2005; 353:487-97, Aug. 4, 2005.
World Health Organization, *Global Tuberculosis Control: A Short Update to the 2009 Report*, 2009.
Super-resolution—Wiklpedia, Oct. 5, 2010.

\* cited by examiner

APPARATUS AND METHOD FOR OBJECT CONFIRMATION AND TRACKING

FIELD OF THE INVENTION

This invention relates generally to a method and apparatus for confirming identification of an object, and more particularly to an apparatus and method for determining an identity of an object through a substantially high accuracy method, and then further tracking the object to continue to confirm its identity using characteristics that may of lesser accuracy. The apparatus and method are most particularly directed to confirming the identity of a medication, such as a medication or other pill to be administered by a user, and thereafter tracking the pill or medication pill or other medication to continue to confirm that the identity of the medication pill or other medication has not changed.

BACKGROUND OF THE INVENTION

Determining an identity of an object through image analysis is a problem that has been addressed through many methods. When applied to a medication pill or the like, one solution is set forth in U.S. patent application Ser. No. 11/839,723. In this application, an image of a pill or the like is taken via a camera on a mobile device. This still image is then analyzed to confirm that the identity of the pill matches a desired identity. Because the pill object is identified through analysis of a still image, continued identity conformation over an elapsed timeframe may be difficult. Any problems associated with that single image, such as bad lighting conditions, occlusions, or the like, may preclude proper identification by not allowing for proper capture of one or more necessary or desired object attributes.

Therefore, it would be desirable to provide an apparatus and system that allow for a more continuous monitoring of the identity of an object, and that overcomes other drawbacks of the prior art.

SUMMARY OF THE INVENTION

In accordance with one or more embodiments of the present invention a method and apparatus are provided that allow for a first, robust determination and confirmation of a medication pill or the like, and thereafter, a less robust determination for confirming that the identity of the medication pill or the like has not changed from the initial confirmation. Both the initial and subsequent determinations are preferably performed based upon a video sequence of images, thus allowing for multiple views of the medication pill or the like, and thus allowing for accurate determination of shape, color, and any additional attributes that may be found useful in determining and confirming the identity of the medication pill or the like. Furthermore, through the user of such multiple images, various occlusions, bad lighting conditions, shadows and the like may be overcome by providing a composite image of the medication to be imaged. In additional embodiments, such an initial determination may include displaying a pill bottle or other medication container including information about the medication, providing a selection of one or more medication pills or other medication from a group of medication to be taken by a user via a pointer, touch screen or other selection method and apparatus, or detecting one of a small number of pills or other medications from a list of medications associated, for example, with a particular user after identification of that user through any appropriate identification technique.

It is further anticipated that the system and method in accordance with the invention may be provided on a computer, mobile device, or other apparatus that may be employed for capturing images of a user administering a medication pill or the like. In particular, this method and apparatus may be employed in conjunction with any method or apparatus described in any one or more of the following co-assigned applications: U.S. patent application Ser. No. 12/620,686, filed Nov. 18, 2009 to Hanina et al. entitled "Method and Apparatus for Verification of Medication Administration Adherence; U.S. patent application Ser. No. 12/646,383, filed Dec. 23, 2009 to Hanina et al. entitled Method and Apparatus for Verification of Clinical Trial Adherence; U.S. patent application Ser. No. 12/646,603, filed Dec. 23, 2009 to Hanina et al. entitled Method and Apparatus for Management of Clinical Trials; U.S. patent application Ser. No. 12/728,721, filed Mar. 22, 2010 to Hanina et al. entitled Apparatus and Method for Collection of Protocol Adherence Data; and U.S. patent application Ser. No. 12/815,037, filed Jun. 14, 2010 to Hanina et al. entitled Apparatus and Method for Recognition of Patient Activities When Obtaining Protocol Adherence Data, the contents of each of these applications being incorporated herein by reference.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION OF THE PREFERRED EMBODIMENTS

Figure 6:
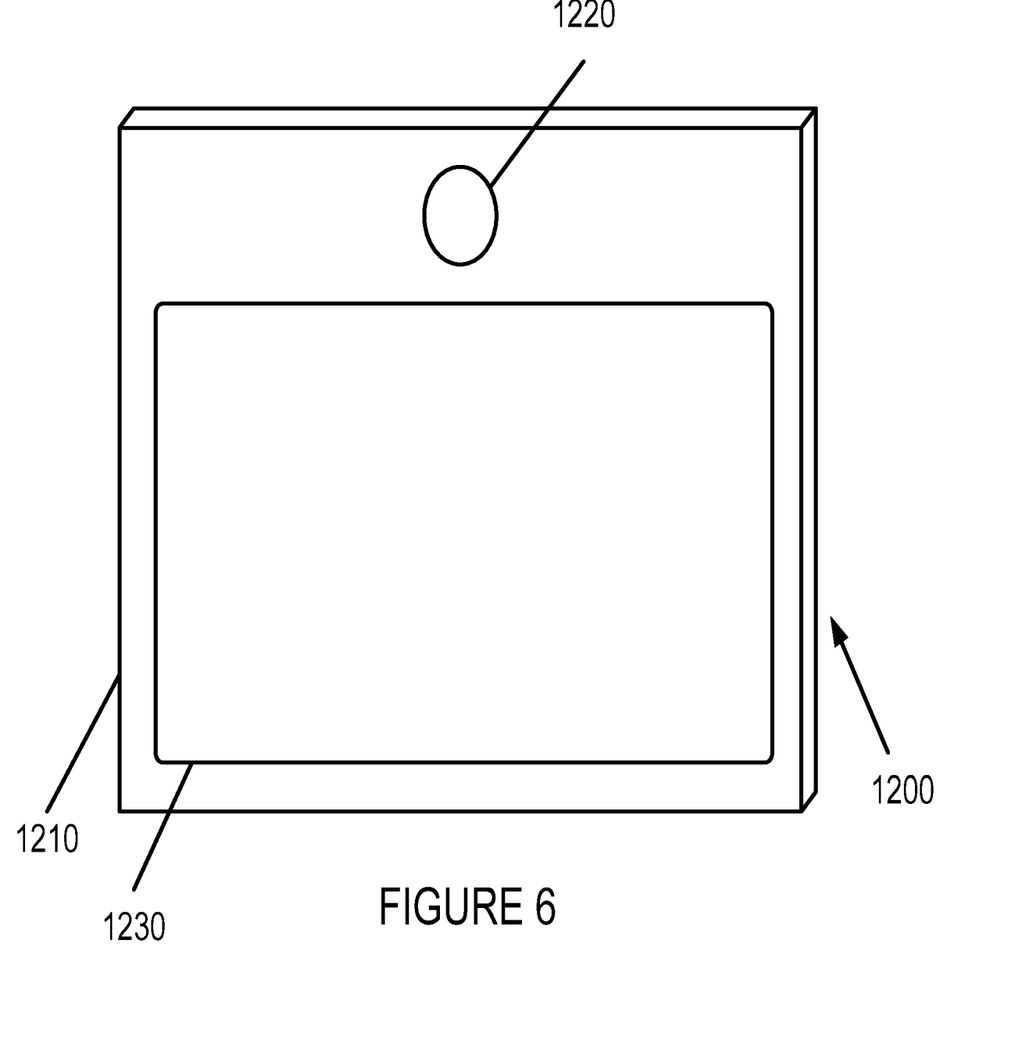
FIG. 6 depicts a display and image capture device that may be employed in accordance with an embodiment of the invention.

The invention will now be described making reference to the following drawings in which like reference numbers denote like structure or steps. Referring first to FIG. 6, a display and image capture apparatus 1200 that may be employed in accordance with one or more embodiments of the present invention is shown. Apparatus 1200 preferably includes a housing 1210, an image capture camera 1220 and a display 1230. Other elements, as known to one of ordinary skill in the art, including ports, power attachments, processors for processing data, and the like may also be provided in accordance with apparatus 1200. The following descriptions of the various embodiments of the invention will assume that such a display and image capture apparatus 1220 is employed. The invention, however, shall not be so limited and may be employed on any structure of image capture camera and display, whether contained in a single or multiple apparatuses. Furthermore, apparatus 1200 may be provided as a mobile, desktop or other standalone device, or may be included as part of an overall system.

Figure 1:
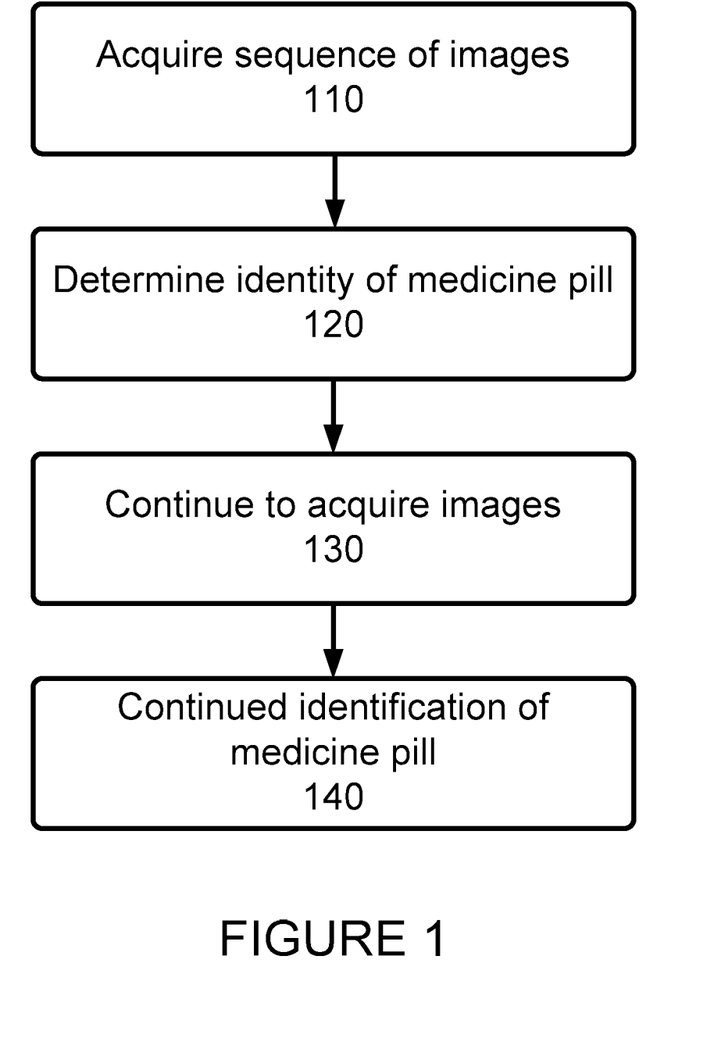
FIG. 1 is a flowchart diagram depicting an overall process flow in accordance with various embodiments of the invention.

Referring next to FIG. 1, a flowchart depicting primary steps in accordance with an embodiment of the invention is shown. As is shown in FIG. 1, first, a sequence of images is acquired of a medicine pill, other medication (such as injectable medication, liquid medication, topical medication and the like) to be administered, or the like at step 110. Through the sequence of images, an identity of the medicine pill may be determined at step 120. This identification may preferably employ a method that may positively identify the medicine pill, such as reading a pill bottle information, barcode reading, positively identifying the shape and/or markings of the pill or one or more other characteristics determined to be characteristically discriminating from other medication pills, other medication to be administered, or the like, or allowing for the indication of a particular pill by a user through selection via a touch screen, mouse, keyboard or keypad, or the like. In this manner, an identity of such a medicine pill may be determined with a high degree of certainty.

Next, after the initial medicine pill identification, images of the pill may continue to be acquired at step 130, and at step 140, these additionally acquired images may be used to continue to confirm the identification of the medicine pill. It is anticipated in accordance with various embodiments of the invention that this continued identification of the medicine pill may require substantially reduced processing and/or imaging power, and therefore may be appropriate for use in reduced processing power systems, such as with mobile devices, or with other applicable systems. Furthermore, a number of inventive methods for performing such identity confirmation in accordance with any of the embodiments of the present invention.

Figure 5:
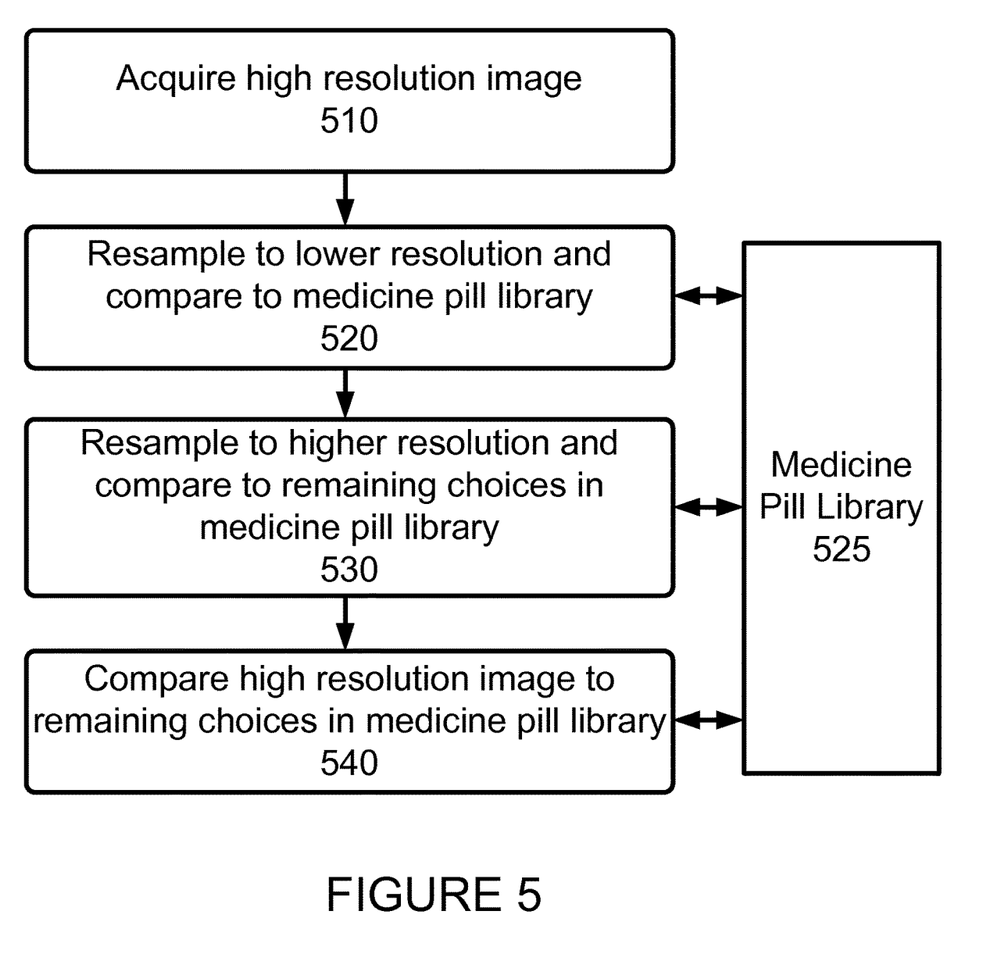
FIG. 5 is a flowchart diagram depicting a multi-scale image recognition process in accordance with an embodiment of the invention.

Multi-Scale Image Recognition—In order to speed processing time and reduce processing overhead to a greatest extent possible, in accordance with various embodiments of the invention, a multi-scale image recognition may be employed when image recognition techniques are to be used to match various characteristics of an imaged pill or other object. Therefore, in accordance with such a process as depicted in FIG. 5, a high resolution image may first acquired at step 510, and then be resampled to a lower resolution at step 520. This lower resolution image may be used to attempt to find or confirm a match with pill or other object information contained in a database or the like, such as medicine pill library 525. This comparison may produce a match, or may reduce a number of possible candidates. For example, consider a situation where an image having a resolution of 200×200 pixels is acquired. In accordance with step 520, the image may be resampled to a 20×20 pixel image, and then compared to entries in medicine pill library 525. If such a database included 1000 possible candidates, comparison of the 20×20 image may exclude 900, and leave only 100 candidates requiring further consideration. Next, at step 530 the original high resolution image may be resampled at a higher pixel rate, and then use for comparison purposes. In our example, the original high resolution image may be resampled at 40×40 pixels and then compared to the remaining 100 possible candidates from medicine pill library 525, perhaps resulting in 50 remaining candidates. This process may be performed for any number of steps, each time providing a higher resolution image. Finally, at step 540, if the lower resolution images are not able to present a single likely candidate, the full high resolution image may be used to compare to the remaining possible candidates in medicine pill library at step 540. In this manner, while resampling must be performed multiple times, the savings in comparison time may initially be great, and result in a faster and more efficient process. Furthermore, it is anticipated that this process may be less sensitive to noise or the scale of any particular image.

Additionally, rather than always searching through an entire library database, it may be possible to first retrieve information about a particular patient, either through password entry, biometric identification, facial recognition, or the like, thus determining an identity of the patient. Thus, the universe of pills to be determined may be reduces to a small set of pills or other medication prescribed to the particular patient. By reducing the possible set of medicines, the ability to differentiate between them will likely be increased as chances are that there will be far fewer pills or medications with very similar identification characteristics. Once a small number of pills or medications have been identified, either through narrowing with low resolution images or patient identification or the like, the user may be queried to confirm that the pill or medication they are to administer is indeed one of the noted pills.

Figure 2:
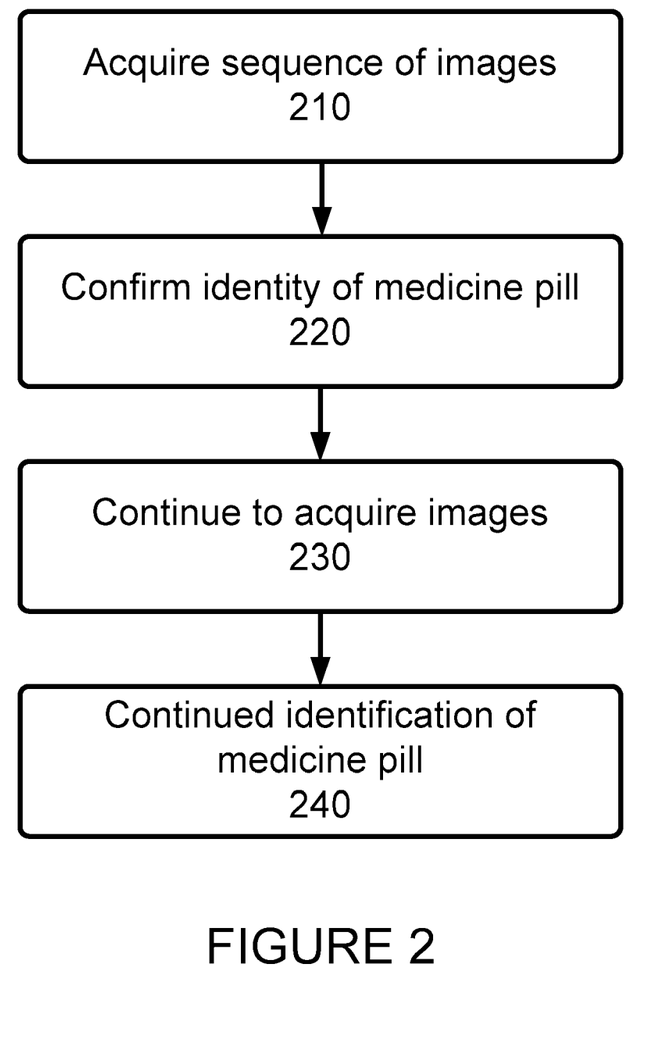
FIG. 2 is a flowchart diagram depicting a process for confirming the identity of a single, known medication pill in accordance with an embodiment of the invention.

Referring next to FIG. 2, a further embodiment of the invention is shown in which it is anticipated that the method and apparatus of this embodiment of the invention has been configured to determine proper administration and ingestion of a particular medication pill. Thus, in accordance with this embodiment of the invention, all characteristics of the medicine pill to be taken are preferably known in advance. Thus, as is shown, at step 210 a sequence of images is acquired of a medicine pill or the like. Through the sequence of images, an identity of the medicine pill may be confirmed at step 220. This identification may preferably employ a method that may positively confirm the identification of the medicine pill, such as reading a pill bottle information, barcode reading, or the like, and comparing such information to a known pill bottle information, positively identifying the shape and/or markings of the pill as compared to the known pill information, or comparing on or more definitive characteristics, comprising a characteristic profile. In this particular embodiment of the invention, because the identity and all characteristics of the medicine pill may be taken are known, determination of the identity of the medication pill may also be performed using one or more attributes, being measured in a binary manner. Thus, the system may confirm a shape match, a color match, a markings match, or the like. Because only one medicine pill may be identified, each of these characteristics may either produce a confirmation or rejection of the attribute. Thus, the system may determine confirmation of the correct medication pill after match indications from a predetermined number of characteristic checks. Alternatively, these attributes or characteristics of the pill may be measured in a manner by determining a value for each of one or more characteristics, thus generating a characteristic profile of the pill. This characteristic profile may be compared to a known characteristic profile of a pill to be administered, and if similar enough, confirmation of the identity of the pill may be confirmed. When employing one or more characteristic profiles, the system may identify, by rankings, which of the attributes are most differentiating for the particular pill, medication or object, and then use these best differentiators for further tracking of the object. In this manner, an identity of such a medicine pill may be determined with a high degree of certainty.

Next, after the initial medicine pill identification, images of the pill may continue to be acquired at step 230, and at step 240, these additionally acquired images may be used to continue to confirm the identification of the medicine pill during medication ingestion. It is anticipated in accordance with various embodiments of the invention that this continued identification of the medicine pill may require substantially reduced processing and/or imaging power, and therefore may be appropriate for use in reduced processing power systems, such as with mobile devices, or with other applicable systems. In accordance with this particular embodiment of the invention, as the medicine pill is known before hand, it may be possible to select a reduced number of attributes to continue to monitor in the additionally acquired images. Thus, by way of example only, if the medication pill is first confirmed using color, shape and markings, as noted above, it may be possible to continue to monitor such medication pill using only color, or perhaps color and shape. Of course, other characteristics may be employed. Therefore, in accordance with this particular embodiment of the invention, a reduced number of characteristics may be used to further track a medication pill that has previously been positively identified. These reduced characteristics may therefore be used to confirm a continued likeness between the initially identified object and the later tracked object, and may therefore determine a likelihood that the currently tracked object is the same as the initially identified object. Of course, which such identification is described related to a medication pill, the invention may be equally applicable to any other medication, regardless of form, or indeed to any other object where initial identification may be performed, and then further tracking of the object to continue to confirm identity of that identified object is desired.

Figure 3:
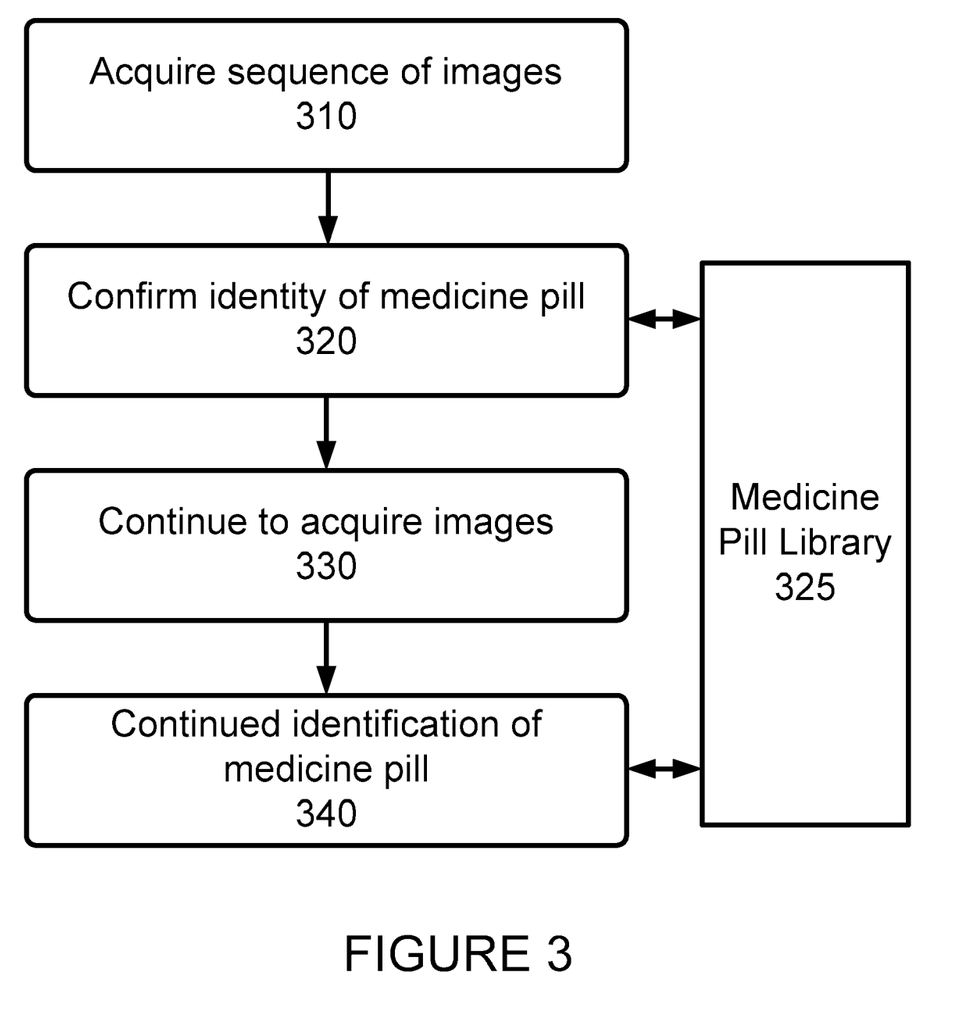
FIG. 3 is a Flowchart diagram depicting a process for determining an identity of a medication pill or the like in accordance with a medicine pill library, in accordance with an embodiment of the invention.

Referring next to FIG. 3, a method in accordance with an additional embodiment of the invention is shown. In this particular embodiment of the invention, it is contemplated that the user may be in a position to have more than one type of medication administered. Thus as is shown in FIG. 3 all characteristics of the medicine pill to be taken are not necessarily known in advance as it is anticipated that the user may be administering one of any number of different medicine pills. Thus, as is shown, at step 310 a sequence of images is acquired of a medicine pill or the like. Through the sequence of images, an identity of the medicine pill may be confirmed at step 320. This identification may preferably employ a method that may positively confirm the identification of the medicine pill, such as reading a pill bottle information, barcode reading or the like, or determining the identity of the pill through one or more known characteristics, and comparing such information to a known pill bottle information, positively identifying the shape and/or markings of the pill as compared to the known pill information. In this particular embodiment of the invention, because the identity and all characteristics of the medicine pill to be taken are not necessarily known ahead of time, a medicine pill library 325 is provided that includes indications of various medicine pill characteristics associated with one or more medicine pills to be administered by a user. Determination of the identity of the medication pill may be performed using one or more attributes, being measured in a continuous type manner. Thus, the system may determine various attributes, such as shape match, color match, markings match, or the like. Thus, in accordance with the invention, a determination of an absolute value representing similarity between a measured and a standard measure of a particular characteristic may be determined. Once performed for each characteristic, these obtained values may be compared to similar values for each characteristic of one or more medicine pills catalogued in medicine pill library 325. Thus, through the use of multivariate comparisons, it may be possible to determine which medicine pill the user has most likely identified. A resulting identification map for the various characteristics may be determined and may be used for later comparisons employing the particular medication pill. The system may determine identification of the presented medication pill after best match indications from a predetermined number of characteristics are determined, or upon employing a best match to all available identification maps. In this manner, an identity of such a medicine pill may be determined with a high degree of certainty.

Once this medication identification has been confirmed, processing may continue to step 330 where images of the medication may continue to be acquired at step 330, and at step 340, these additionally acquired images may be used to continue to confirm the identification of the medicine. It is anticipated in accordance with various embodiments of the invention that this continued identification of the medicine may require substantially reduced processing and/or imaging power, and therefore may be appropriate for use in reduced processing power systems, such as with mobile devices, or with other applicable systems. In accordance with this particular embodiment of the invention, comparison of the various characteristics of the one or more pills that may be administered by the user from medicine pill library 325 may result in one or more of the characteristic being most different from the characteristics of the other pills, and therefore tracking of this one or more characteristics may provide sufficient differentiation from other of the pills to be administered so that the continued tracking of such pill may be confirmed monitoring only this reduced set of characteristics. Through such a reduced set of characteristics, likeness of the initially identified medication and the currently tracked medication can be confirmed. Thus, by way of example only, if the medication pill may be first identified using color, shape and markings, as noted above, it may be possible to continue to monitor such medication pill using only color, or perhaps color and shape if the color of the pill to be administered is close to the color of another pill that is not yet being, or has already been administered. Of course, other characteristics may be employed. Therefore, in accordance with this particular embodiment of the invention, a reduced number of characteristics may be used to further track a medication pill that has previously been positively identified. Through the use of multiple subsequent images, good data related to each of the characteristics that is being tracked may be obtained, as will be described below.

In accordance with the various embodiments of the present invention the benefits of determining, confirming and tracking a medication pill using video sequences are substantial. First, through the user of sequential images, multiple views of an object such as a medication pill may be obtained, and thus any effects of shadows, occlusion, or other factors potentially effecting capture of a single image may be removed through various averaging or other techniques. Indeed, a three-dimensional representation of the medication may be generated in accordance with information obtained from multiple images. Additionally, various techniques, such a super resolution or the like may be employed. Such a multi frame super resolution technique is well known to those of ordinary skill in the art and is frequently used to enhance the visual appearance of an image. In accordance with this embodiment of the invention, it is suggested that such super resolution may be used to improve identification used herein. Thus, through the user of multiple captured frames, and various pixel shifting techniques, such super resolution may be employed where it is determined likely to be of benefit.

Furthermore, the identity of the object such as the medication pill may be continuously monitored as it is moved through the administration sequence, as in accordance with the various embodiments of the present invention, a reduced set of characteristics may be monitored, thus speeding processing time, and also allowing for more flexible tracking options. Additionally, if various characteristics cannot be determined despite using multiple images, changes to the environment may be provided, such as providing strobe or other supplemental lighting, requests for different positioning of the object, requesting that the user move to a different location or alter the ambient lighting conditions, and perhaps requiring a reacquisition of all of the parameters, back in the initial medication pill identification step.

While the features of this invention have been described to identifying and further continued confirmation of the identity of a medication pill, such features of the invention may be equally applicable to other objects, and even to various facial recognition techniques. When used with such facial recognition, a user may first be asked to record a short video of themselves, which is preferably not stored, but may be used to create a profile. This profile may then be used to match with any future facial images for recognition, and indeed, as noted above, a reduced characteristic set may be employed once an initial identification is confirmed. Also it may be possible to employ with a pass code, voice recognition or the like to aid in initial and subsequent identification sequences, if lighting conditions make such identification difficult. Alternatively, either of these additional features may be used independently, having the features of the various embodiments of the invention applied thereto.

Figure 4:
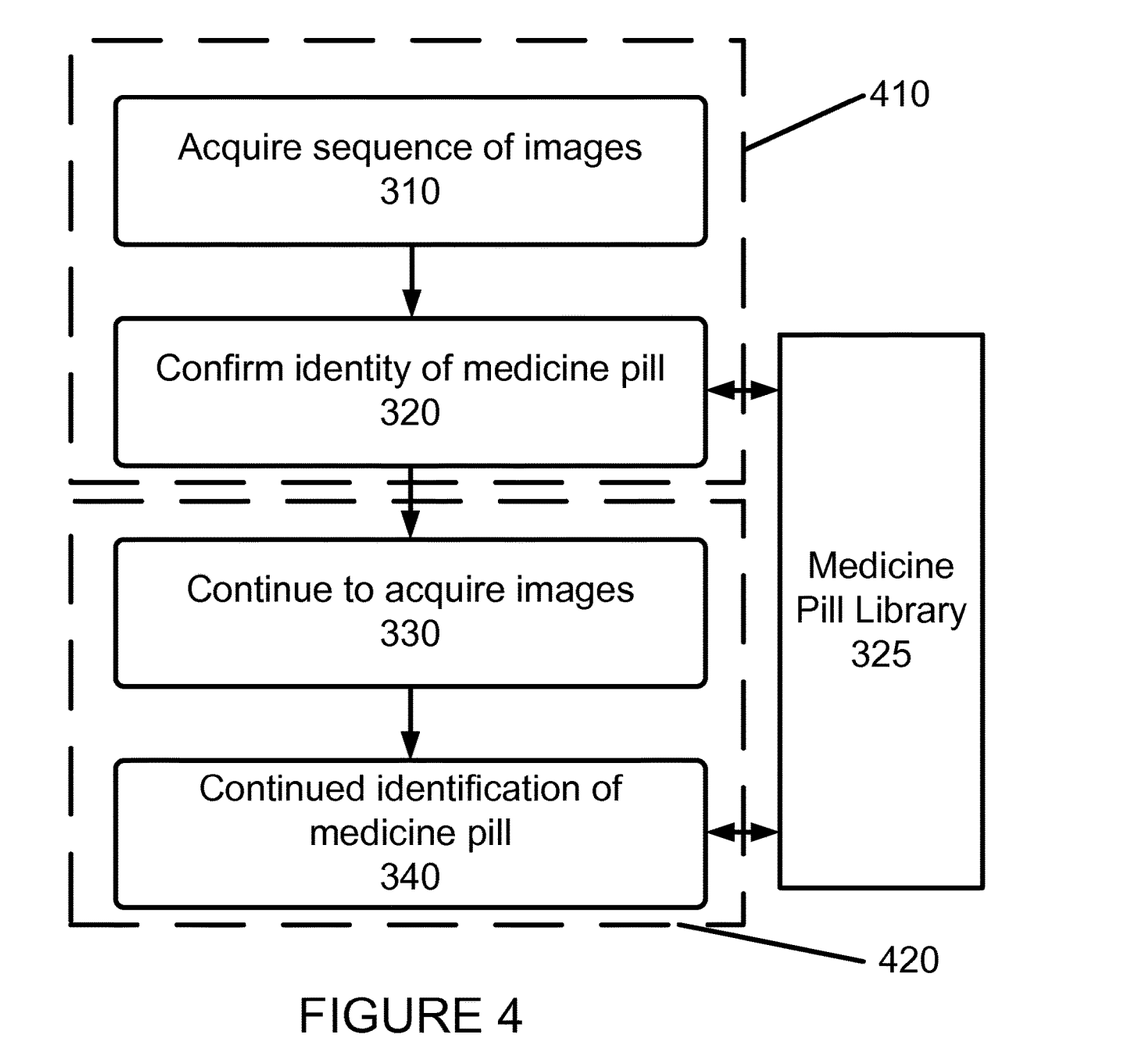
FIG. 4 is a flowchart diagram depicting a process for determining an identity of a medication pill or the like, including resolution toggling, in accordance with an embodiment of the invention.

In an additional embodiment of the present invention, recognition is made that that the ability to reduce the amount of computing resources used for object tracking may be available. Thus, by way of example, during an initial identification phase, substantial computing resources may be necessary to initially identify an object, while once positively identified, fewer computing resources may be necessary to confirm that the identity of an object has not changed. Thus, as is shown in FIG. 4, a method for applying such resolution toggling is shown. As is set forth in FIG. 4 by way of example only, a first processing requirement 410 encompasses steps 310 and 320 of FIG. 3. Thus, during initial medicine pill recognition, maximum computing power may be required to provide a greatest number of captured images for processing and the like. Thereafter, at 420, when merely tracking to be sure that the object does not change, a reduced resolution and computing resources may be required, thus permitting the system resources to be utilized elsewhere, such as in processing locations of elements being tracked or the like. Additionally, if it is further determined that various instances of increased resolution may be required, it may be possible to locally increase resolution within an image, thus providing increased detection ability about a desired area in sequence of images while leaving a reduced resolution for a remaining portion of the image areas.

It is further contemplated in accordance with various further embodiments of the invention that the imaging apparatus and inventive method may be also adaptive based upon one or more determined environmental conditions. Thus, if after initial identification it is determined, for example, that tracking based upon color of a medication is desirable, determining a change in lighting conditions may be important. Thus, if the ambient light level is reduced, it may be determined that another feature of the medication fingerprint may be easier to track, such as shape of the pill. Thus, in accordance with the various embodiments of the invention, determination of a best characteristic of a medication profile may not be absolute, and indeed, the selection or continued use of such a characteristic may be dynamic based upon internal or external conditions.

In an alternative embodiment of the invention, if a medication pill is provided that, for whatever reason, the medication pill cannot be properly imaged, the user may be encouraged to use a medication cup associated with the medication pill. Such a cup may also be employed when a liquid medication is employed. Such a cup may be used for identification, or alternatively, the user may be able to show the pill in the cup to the imaging device, thus improving imaging processing as the color of the inside of the cup will be known. When using a liquid medication, color may be the only characteristic outside of the bottle that may be detected. Additionally, medication may be tracked from a user's hand to a cup or other container, and then the container may be tracked. In such a situation, it may be desirable to first determine the identity of the medication, then continue to track it, and further to determine the identity of the container, and then continue to track it, using the various embodiments of the invention described above. It may also be possible to further image the medication within the hand or cup, using this composite image for initial identification and subsequent tracking.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description is intended to cover all of the generic and specific features of the invention herein described and all statements of the scope of the invention which, as a matter of language, might be said to fall there between.

What is claimed:

1. A computer-implemented method for tracking a medication while the medication is administered by a user, comprising:

capturing, by an image capture device, at least one image of the medication as the user performs one or more steps associated with the administration of the medication;

upon capturing the at least one image, identifying, by a computing device, a plurality of tracking characteristics associated with the medication from the at least one captured image, by applying one or more image recognition techniques to the at least one captured image;

determining, by the computing device, the identity of the medication being administered by the user from the identified plurality of tracking characteristics during performance by the user of one or more steps associated with administration of the medication;

identifying, by the computing device, a reduced set of the tracking characteristics that are to be used to continue to track the medication during performance by the user of subsequent steps associated with administration of the medication, wherein the subsequent steps comprise at least ingestion of the medication;

capturing, by the image capture device, at least one additional image of the medication as the user performs the subsequent steps associated with the administration of the medication; and tracking, by the computing device, the medication within the at least one additional image based on identification of the reduced set of tracking characteristics within the at least one additional image, as the user performs the subsequent steps associated with the administration of the medication, including at least confirmation of ingestion of the medication.

2. The method of claim 1, wherein determining the identity of the medication being administered by the user further comprises:

determining at least one value for each tracking characteristic of the plurality of tracking characteristics;

comparing, for each tracking characteristic, the determined at least one value to a corresponding predetermined threshold; and confirming the identity of the medication when a predetermined number of values of the tracking characteristics of the medication pass the corresponding predetermined thresholds.

3. The method of claim 1, wherein determining the identity of the medication being administered by the user further comprises imaging the identity from one or more indicators contained on a pill bottle.

4. The method of claim 1, wherein the medication being administered by the user is one of a predetermined number of medications that may be administered by the user.

5. The method of claim 4, wherein determining the identity of the medication being administered by the user further comprises:

determining, for each tracking characteristic of the plurality of tracking characteristics, at least a first corresponding value to generate a characteristic profile of the medication;

comparing the generated characteristic profile to one or more predetermined characteristic profile models, each of the predetermined characteristic profile models being associated with a corresponding medication from the predetermined number of medications; and confirming the identity of the medication by selecting a medication associated with the characteristic profile model determined to be a closest match to the generated characteristic profile.

6. The method of claim 5, further comprising generating one or more super resolution images from the at least one captured image;

wherein the generated characteristic profile is generated from the one or more super resolution images.

7. The method of claim 5, further comprising:

sampling, by the computing device, the at least one captured image to reduce the resolution thereof to generate at least one low resolution image;

wherein the at least first corresponding value for each tracking characteristic is determined from the at least one low resolution image.

8. The method of claim 7, further comprising:

sampling, by the computing device, the at least one captured image to reduce the resolution thereof to generate at least one medium resolution image having a resolution higher than the at least one low resolution image;

determining, for each tracking characteristic of the plurality of tracking characteristics, at least a second corresponding value from the at least one medium resolution image to generate a second characteristic profile of the medication; and comparing the second characteristic profile to the one or more predetermined characteristic profile models, wherein confirming the identity of the medication further comprises selecting a medication from the predetermined number of medications having a medication profile model determined to be a sufficiently close match to the generated second characteristic profile.

9. An apparatus for tracking a medication while being administered by a user, the apparatus comprising:

an image capture apparatus operable to capture at least one image of the medication being administered by the user; and a processor operable to identify, from the at least one image, a plurality of tracking characteristics associated with the medication by applying one or more image recognition techniques to the at least one image, determine the identity of the medication being administered by the user during performance by the user of one or more steps associated with administration of the medication, identify a reduced set of the tracking characteristics that are to be used to continue to track the medication during performance by the user of subsequent steps associated with administration of the medication, wherein the subsequent steps comprise ingestion of the medication; and track the medication, as the user performs the subsequent steps associated with the administration of the medication, including at least confirmation of ingestion of the medication, within at least one additional image captured by the image capture device based on identification of the reduced set of tracking characteristics in the at least one additional image.

10. The apparatus of claim 9, wherein the processor is operable to determine the identity of the medication by performing operations comprising:

determining at least one value for each tracking characteristic of the plurality of tracking characteristics;

comparing, for each tracking characteristic, the determined at least one value to a corresponding predetermined threshold, and confirming the identity of the medication when a predetermined number of values of the tracking characteristics of the medication pass the corresponding predetermined thresholds.

11. The apparatus of claim 9, wherein the image capture apparatus is operable to capture one or more images of a pill bottle associated with the medication being administered, and the processor is further operable to determine the identity of the medication being administered by the user from one or more indicators contained on the pill bottle.

12. The apparatus of claim 9, wherein the medication being administered by the user is one of a predetermined number of medications that may be administered by the user.

13. The apparatus of claim 12, wherein the processor is operable to determine the identity of the medication being administered by the user by performing operations comprising:
   determining, for each tracking characteristic of the plurality of tracking characteristics, at least a first corresponding value to generate a characteristic profile of the medication;
   comparing the generated characteristic profile to one or more predetermined characteristic profile models, each of the predetermined characteristic profile models being associated with a corresponding medication from the predetermined number of medications; and
   confirming the identity of the medication by selecting a medication associated with the characteristic profile model determined to be a closest match to the generated characteristic profile.

14. The apparatus of claim 13, wherein the processor is further operable to generate one or more super resolution images from the at least one captured image, and to generate the characteristic profile from the one or more super resolution images.

15. The apparatus of claim 13, wherein the processor is further operable to:
   sample the at least one captured image to reduce the resolution thereof to generate at least one low resolution image,
   determine the at least first corresponding value for each tracking characteristic from the at least one low resolution image.

16. The apparatus of claim 15, wherein the processor is further operable to:
   sample the at least one captured image to reduce the resolution thereof to generate at least one medium resolution image having a resolution higher than the at least one low resolution image;
   determine for each tracking characteristic of the plurality of tracking characteristics, at least a second corresponding value from the at least one medium resolution image to generate a second characteristic profile of the medication; and
   compare the second characteristic profile to the one or more predetermined characteristic profile models,
   wherein confirming the identity of the medication comprises selecting a medication from the predetermined number of medications having a medication profile model determined to be a sufficiently close match to the second generated characteristic profile.

17. A computer program, for tracking a medication while being administered by a user, stored to a computer readable medium and operable on a computing device, the computing device further including an image capture camera and a display, the computer program causing the computing device to perform the actions of:
   identifying, from at least one image of the medication captured by the image capture camera, a plurality of tracking characteristics associated with the medication by applying one or more image recognition techniques to the at least one image;
   determining, as the user performs one or more steps associated with the administration of the medication, the identity of the medication being administered from the identified plurality of tracking characteristics;
   identifying a reduced set of the tracking characteristics that are to be used to continue to track the medication through subsequent images acquired by the image capture camera during performance by the user of subsequent steps associated with administration of the medication, wherein the subsequent steps comprise at least ingestion of the medication; and
   tracking the medication within at least one additional image captured by the image capture camera, based on identification of the reduced set of tracking characteristics in the at least one additional image, as the user performs the subsequent steps associated with the administration of the medication, including at least confirmation of ingestion of the medication.

18. The computer program of claim 17, wherein determining the identity of the medication being administered by the user further comprises:
   capturing, with the image capture camera, the at least one additional image;
   determining at least one value for each tracking characteristic of the plurality of tracking characteristics;
   comparing, for each tracking characteristic, the determined at least one value to a corresponding predetermined threshold and
   confirming the identity of the medication when a predetermined number of values of the tracking characteristics of the medication pass the corresponding predetermined thresholds.

19. The computer program of claim 17, wherein determining the identity of the medication being administered by the user further comprises imaging the identity from one or more indicators contained on a pill bottle.

20. The computer program of claim 17, wherein the medication being administered by the user is one of a predetermined number of medications that may be administered by the user.

21. The computer program of claim 20, wherein determining the identity of the medication being administered by the user further comprises:
   determining, for each tracking characteristic of the plurality of tracking characteristics, at least a first corresponding value to generate a characteristic profile of the medication;
   comparing the generated characteristic profile to one or more predetermined characteristic profile models, each of the predetermine characteristic profile models being associated with a corresponding medication from the predetermined number of medications; and
   confirming the identity of the medication by selecting a medication associated with the characteristic profile model determined to be a closest match to the generated characteristic profile.

22. The computer program of claim 21, wherein the computer program is further operable to cause the computing device to perform actions that comprise:
   generating one or more super resolution images from the at least one captured image;
   wherein the generated characteristic profile is generated from the one or more super resolution images.

23. The computer program of claim 21, wherein the computer program is further operable to cause the computing device to perform actions that comprise:
   sampling the at least one captured image to reduce the resolution thereof to generate at least one low resolution image;
   wherein the at least first corresponding value for each tracking characteristic is determined from the at least one low resolution image.

24. The computer program of claim 23, wherein the computer program is further operable to cause the computing device to perform actions that comprise:

Sampling the at least one captured image to reduce the resolution thereof to generate at least one medium resolution image having a resolution higher than the at least one low resolution image;

determining for each tracking characteristic of the plurality of tracking characteristics, at least a second corresponding value from the at least one medium resolution image to generate a second characteristic profile of the medication; and comparing the second characteristic profile to the one or more predetermined characteristic profile models, wherein confirming the identity of the medication further comprises selecting a medication from the predetermined number of medications having a medication profile model determined to be a sufficiently close match to the generated second characteristic profile.

25. The method of claim 7, wherein the medication being administered by the user comprises at least two of a predetermined number of medications that may be administered by the user, and wherein confirming the identity of the medication further comprises identifying, from the predetermined number of medications that may be administered by the user, the at least two medications that each have a corresponding profile that is a sufficiently close match to the generated characteristic profile to form a potential group of medications.

* * * * *